(12) United States Patent
Sanborn et al.

(10) Patent No.: US 10,991,451 B2
(45) Date of Patent: *Apr. 27, 2021

(54) BAMBAM: PARALLEL COMPARATIVE ANALYSIS OF HIGH-THROUGHPUT SEQUENCING DATA

(71) Applicant: THE REGENTS OF THE UNIVERSITY OF CALIFORNIA, Oakland, CA (US)

(72) Inventors: John Zachary Sanborn, Santa Cruz, CA (US); David Haussler, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 16/107,745

(22) Filed: Aug. 21, 2018

(65) Prior Publication Data

US 2018/0357369 A1    Dec. 13, 2018

Related U.S. Application Data

(63) Continuation of application No. 15/634,919, filed on Jun. 27, 2017, now Pat. No. 10,268,800, which is a
(Continued)

(51) Int. Cl.
*G16B 30/10* (2019.01)
*G16B 20/20* (2019.01)
(Continued)

(52) U.S. Cl.
CPC .......... *G16B 20/20* (2019.02); *C12Q 1/6886* (2013.01); *G06F 3/04845* (2013.01);
(Continued)

(58) Field of Classification Search
CPC .......... G06F 19/22; G06N 7/005; G16B 30/10
See application file for complete search history.

(56) References Cited

U.S. PATENT DOCUMENTS

| 4,736,866 A | 4/1988 | Leder et al. |
| 5,175,383 A | 12/1992 | Leder et al. |

(Continued)

FOREIGN PATENT DOCUMENTS

| CN | 1536068 | 10/2004 |
| CN | 1645401 | 7/2005 |

(Continued)

OTHER PUBLICATIONS

Li et al., "Mapping short DNA sequencing reads and calling variants using mapping 19 quality score." Genome research 18.11 1851-1858. (Year: 2008).*

(Continued)

*Primary Examiner* — Paulinho E Smith
(74) *Attorney, Agent, or Firm* — Kilpatrick Townsend & Stockton LLP

(57) ABSTRACT

The present invention relates to methods for evaluating and/or predicting the outcome of a clinical condition, such as cancer, metastasis, AIDS, autism, Alzheimer's, and/or Parkinson's disorder. The methods can also be used to monitor and track changes in a patient's DNA and/or RNA during and following a clinical treatment regime. The methods may also be used to evaluate protein and/or metabolite levels that correlate with such clinical conditions. The methods are also of use to ascertain the probability outcome for a patient's particular prognosis.

19 Claims, 5 Drawing Sheets

Related U.S. Application Data continuation of application No. 15/167,530, filed on May 27, 2016, now Pat. No. 9,721,062, which is a continuation of application No. 13/134,047, filed on May 25, 2011, now Pat. No. 9,652,587.

(60) Provisional application No. 61/396,356, filed on May 25, 2010.

(51) Int. Cl.

| | | |
|---|---|---|
| *G16B 30/00* | (2019.01) | |
| *G16H 50/20* | (2018.01) | |
| *G06F 40/169* | (2020.01) | |
| *G16B 40/00* | (2019.01) | |
| *G06F 3/0484* | (2013.01) | |
| *G06T 11/20* | (2006.01) | |
| *G06N 7/00* | (2006.01) | |
| *C12Q 1/6886* | (2018.01) | |
| *G16H 70/20* | (2018.01) | |
| *G16H 10/40* | (2018.01) | |
| *G16H 10/60* | (2018.01) | |

(52) U.S. Cl.
CPC .......... *G06F 40/169* (2020.01); *G06N 7/005* (2013.01); *G06T 11/206* (2013.01); *G16B 30/00* (2019.02); *G16B 30/10* (2019.02); *G16B 40/00* (2019.02); *G16H 50/20* (2018.01); *C12Q 2600/106* (2013.01); *C12Q 2600/118* (2013.01); *C12Q 2600/156* (2013.01); *G06F 2203/04806* (2013.01); *G16H 10/40* (2018.01); *G16H 10/60* (2018.01); *G16H 70/20* (2018.01); *Y02A 90/10* (2018.01); *Y02A 90/30* (2018.01)

(56) References Cited

U.S. PATENT DOCUMENTS

| | | |
|---|---|---|
| 5,767,337 A | 6/1998 | Roses et al. |
| 6,236,993 B1 | 5/2001 | Fanberg |
| 6,346,381 B1 | 2/2002 | Cohen et al. |
| 6,355,423 B1 | 3/2002 | Rothberg et al. |
| 6,389,428 B1 | 5/2002 | Rigault et al. |
| 6,982,145 B1 | 1/2006 | Mercola et al. |
| 7,700,359 B2 | 4/2010 | Chan et al. |
| 8,140,270 B2 | 3/2012 | Kingsmore et al. |
| 8,340,914 B2 | 12/2012 | Gatewood et al. |
| 8,700,430 B2 | 4/2014 | Miller et al. |
| 8,751,100 B2 | 6/2014 | Johnson et al. |
| 9,092,401 B2 | 7/2015 | Richards et al. |
| 9,165,109 B2 | 10/2015 | Chaisson |
| 9,646,134 B2 | 5/2017 | Sanborn et al. |
| 9,646,550 B2 | 5/2017 | Kim et al. |
| 9,652,587 B2 | 5/2017 | Sanborn et al. |
| 9,721,062 B2 | 8/2017 | Sanborn et al. |
| 9,824,181 B2 | 11/2017 | Sanborn et al. |
| 10,242,155 B2 | 3/2019 | Sanborn et al. |
| 10,249,384 B2 | 4/2019 | Sanborn et al. |
| 10,268,800 B2 | 4/2019 | Sanborn et al. |
| 10,726,945 B2 | 7/2020 | Sanborn et al. |
| 10,825,551 B2 | 11/2020 | Sanborn et al. |
| 10,825,552 B2 | 11/2020 | Sanborn et al. |
| 2003/0003463 A1 | 1/2003 | Rothberg et al. |
| 2003/0046114 A1 | 3/2003 | Davies et al. |
| 2003/0180717 A1* | 9/2003 | Esteban ............... C12Q 1/70 435/5 |
| 2003/0183268 A1 | 10/2003 | Shanefield |
| 2004/0015298 A1 | 1/2004 | Swindells et al. |
| 2004/0153255 A1* | 8/2004 | Ahn ...................... G16B 30/00 702/20 |
| 2005/0079504 A1 | 4/2005 | Amitai et al. |
| 2006/0271309 A1 | 11/2006 | Showe et al. |
| 2007/0010469 A1 | 1/2007 | Chan et al. |
| 2007/0166707 A1 | 7/2007 | Schadt et al. |
| 2007/0178474 A1 | 8/2007 | Cracauer et al. |
| 2008/0077607 A1 | 3/2008 | Gatawood et al. |
| 2008/0126117 A1 | 5/2008 | Miller et al. |
| 2009/0112439 A1 | 4/2009 | Kuang et al. |
| 2009/0183268 A1* | 7/2009 | Kingsmore ........ A61K 31/7088 514/1.1 |
| 2009/0299645 A1 | 12/2009 | Colby et al. |
| 2010/0041037 A1 | 2/2010 | Gudmundsson et al. |
| 2010/0092964 A1 | 4/2010 | Zabeau et al. |
| 2010/0331209 A1 | 12/2010 | Huang et al. |
| 2011/0098193 A1* | 4/2011 | Kingsmore .......... C12Q 1/6869 506/9 |
| 2012/0041638 A1 | 2/2012 | Johnson et al. |
| 2012/0041683 A1* | 2/2012 | Vaske ................... G16B 5/20 702/19 |
| 2012/0059594 A1 | 3/2012 | Hatchwell et al. |
| 2012/0059670 A1* | 3/2012 | Sanborn ................ G16B 30/00 705/3 |
| 2012/0066001 A1* | 3/2012 | Sanborn ................ G16B 50/00 705/3 |
| 2012/0089339 A1 | 4/2012 | Ganeshalingam et al. |
| 2012/0116688 A1 | 5/2012 | Mishra et al. |
| 2012/0330566 A1* | 12/2012 | Chaisson ............... G16B 30/00 702/20 |
| 2013/0073217 A1* | 3/2013 | Dewey ................... G16B 40/00 702/20 |
| 2013/0275023 A1 | 10/2013 | Gregg et al. |
| 2013/0306923 A1 | 11/2013 | Hua |
| 2014/0121116 A1* | 5/2014 | Richards ............... G16B 30/00 506/2 |
| 2014/0287934 A1* | 9/2014 | Szelinger ............... G16B 30/00 506/2 |
| 2014/0371109 A1* | 12/2014 | McMillen ............. H01L 23/528 506/38 |
| 2015/0045988 A1 | 2/2015 | Gusikhin et al. |
| 2015/0141391 A1* | 5/2015 | Chinnaiyan ...... C07K 14/70567 514/182 |
| 2016/0180019 A1* | 6/2016 | Van Rooyen .......... G16B 40/00 702/19 |
| 2016/0306922 A1* | 10/2016 | van Rooyen ....... G06F 19/3418 |
| 2016/0306923 A1* | 10/2016 | van Rooyen .......... G16B 40/00 |

FOREIGN PATENT DOCUMENTS

| | | |
|---|---|---|
| CN | 101539967 | 9/2009 |
| CN | 102007220 A | 4/2011 |
| CN | 102177436 | 9/2011 |
| EP | 1152349 A1 | 11/2001 |
| JP | 0231699 | 2/1990 |
| JP | 2003099440 | 4/2003 |
| JP | 2003527855 | 9/2003 |
| JP | 2004501669 | 1/2004 |
| JP | 2004529650 | 9/2004 |
| JP | 2008526775 | 7/2008 |
| JP | 2008182993 | 8/2008 |
| JP | 2009532664 | 9/2009 |
| JP | 2010204838 | 9/2010 |
| JP | 6387070 | 8/2018 |
| JP | 6539835 | 6/2019 |
| KR | 20040031291 | 4/2004 |
| KR | 20040070438 | 8/2004 |
| KR | 101947225 | 2/2019 |
| KR | 101952965 | 2/2019 |
| WO | 9740462 A2 | 10/1997 |
| WO | 0170948 A2 | 9/2001 |
| WO | 02061659 | 8/2002 |
| WO | 2011139345 | 11/2011 |
| WO | 2011149534 | 12/2011 |

OTHER PUBLICATIONS

Quinlan et al., "BEDTools: a flexible suite of utilities for comparing genomic features." 15 Bioinformatics 26.6 : 841-842 (Year: 2010).*

Kraus et al., "A position 12-activated H-ras oncogene in all HS578T 17 mammary carcinosarcoma cells but not normal mammary cells

(56) References Cited

OTHER PUBLICATIONS of the same patient." Proceedings of the National Academy of Sciences 81.17 : 5384-5388. (Year: 1984).*
Choi et al., "Genetic diagnosis by whole exome capture and massively parallel DNA sequencing." Proceedings of the National Academy of Sciences 106.45 : 19096-19101. (Year: 2009).*
Thompons et al., "A Comprehensive Comparison of Multiple Sequence Alignment Programs", 1999, Nucleic Acids Research, vol. 27 No. 13, pp. 2682-2690. (Year: 1999).*
CA2,854,084, "Notice of Allowance", dated Jun. 20, 2019, 1 page.
CN201611137830.4, "Office Action", dated Jun. 20, 2019, 7 pages.
KR10-2016-7014294, "Notice of Decision to Grant", dated Jul. 31, 2019, 3 pages.
KR10-2016-7014294, "Office Action", dated May 20, 2019, 3 pages.
KR10-2019-7005017, "Notice of Decision to Grant", dated Jul. 31, 2019, 3 pages.
KR10-2019-7005017, "Office Action", dated May 20, 2019, 3 pages.
U.S. Appl. No. 14/567,774, "Notice of Allowance", dated Dec. 19, 2018, 9 pages.
U.S. Appl. No. 15/167,528, "Corrected Notice of Allowability", dated Dec. 18, 2018, 4 pages.
U.S. Appl. No. 15/634,919, "Notice of Allowance", dated Dec. 10, 2018, 5 pages.
AU2016203450, "First Examination Report", dated Dec. 21, 2018, 4 pages.
AU2016210784, "First Examination Report", dated Jan. 3, 2019, 5 pages.
CN201611137830.4, "Office Action", dated Nov. 2, 2018, 31 pages.
Hua et al., "An Evolutionary Model for Maximum Likelihood Alignment of DNA Sequences", Chinese Master's Theses Full-text Database, Information Science and Technology (Monthly), No. 7, Jul. 2009, pp. 1-22.
IL232512, "Office Action", dated Dec. 12, 2018, 6 pages.
JP2017-251051, "Office Action", dated Nov. 14, 2018, 6 pages.
KR10-2012-7033515, "Notice of Decision to Grant", dated Nov. 21, 2018, 3 pages.
Ley et al., "DNA Sequencing of a Cytogenetically Normal Acute Myeloid Leukaemia Genome", Nature, vol. 456, No. 7218, Nov. 6, 2008, pp. 1-16.
Li et al., "A Survey of Sequence Alignment Algorithms for Next-Generation Sequencing", Briefings in Bioinformatics, vol. 11, No. 5, May 11, 2010, pp. 473-483.
Li et al., "The Sequence Alignment/Map Format and SAM Tools", Bioinformatics, vol. 25, No. 16, Jun. 8, 2009, pp. 2078-2079.
Mardis et al., "Cancer Genome Sequencing: a Review", Human Molecular Genetics, vol. 18, Issue 2, 2009, pp. 163-168.
JP2017-251051, "Notice of Decision to Grant", dated Apr. 10, 2019, 3 pages.
JP2017-251051, "Office Action", dated Mar. 6, 2019, 6 pages.
U.S. Appl. No. 15/167,507, "Non-Final Office Action", dated May 1, 2020, 21 pages.
U.S. Appl. No. 15/808,722, "Corrected Notice of Allowability", dated Apr. 1, 2020, 2 pages.
CA2,797,645, "Notice of Allowance", dated Apr. 14, 2020, 1 page.
EP19201104.7, "Extended European Search Report", dated Apr. 17, 2020, 11 pages.
Glez-Pena et al., "Pileline: A Toolbox to Handle Genome Position Information in Next-Generation Sequencing Studies", BMC Bioinformatics, vol. 12, No. 31, Jan. 24, 2011, 4 pages.
Goya et al., "SNVmix: Predicting Single Nucleotide Variants from Next-Generation Sequencing of Tumors", Bioinformatics, vol. 26, No. 6, Mar. 15, 2010, pp. 730-736.
"Manual Reference Pages", Samtools Available Online at:https://web.archive.org/web/20110925013941/http://samtools.sourceforge.net/samtools.shtml, Dec. 24, 2019, 9 pages.
"Somatic Mutation Calling", Varscan Available online at: https://web.archive.org/web/20110922134931/http://varscan.sourceforge.net/somaticcalling.html#somatic-input, Sep. 22, 2011, 5 pages.
U.S. Appl. No. 15/808,722, "Notice of Allowance", dated Dec. 3, 2019, 5 pages.
AU2016203450, "Third Examination Report", dated Dec. 10, 2019, 4 pages.
AU2016210784, "Third Examination Report", dated Dec. 18, 2019, 6 pages.
IL251515, "Office Action", dated Dec. 26, 2019, 7 pages.
JP2018-151206, "Office Action", dated Nov. 27, 2019, 6 pages.
U.S. Appl. No. 13/134,047, "Final Office Action", dated Jan. 27, 2014, 29 pages.
U.S. Appl. No. 13/134,047, "Final Office Action", dated Jun. 4, 2015, 33 pages.
U.S. Appl. No. 13/134,047, "Non-Final Office Action", dated Oct. 23, 2014, 28 pages.
U.S. Appl. No. 13/134,047, "Non-Final Office Action", dated Jul. 5, 2013, 29 pages.
U.S. Appl. No. 13/134,047, "Notice of Allowance", dated Jan. 12, 2017, 18 pages.
U.S. Appl. No. 13/134,047, "Restriction Requirement", dated May 1, 2013, 8 pages.
U.S. Appl. No. 13/137,047, "Advisory Action", dated Jun. 23, 2014, 6 pages.
U.S. Appl. No. 13/373,550, "Final Office Action", dated Jun. 4, 2015, 32 pages.
U.S. Appl. No. 13/373,550, "Non-Final Office Action", dated Oct. 23, 2014, 32 pages.
U.S. Appl. No. 13/373,550, "Notice of Allowance", dated Dec. 30, 2016, 28 pages.
U.S. Appl. No. 13/373,550, "Restriction Requirement", dated Jul. 9, 2014, 8 pages.
U.S. Appl. No. 14/567,774, "Final Office Action", dated Oct. 31, 2017, 33 pages.
U.S. Appl. No. 14/567,774, "Non Final Office Action", dated May 24, 2017, 35 pages.
U.S. Appl. No. 15/167,507, "Final Office Action", dated Jul. 10, 2017, 33 pages.
U.S. Appl. No. 15/167,507, "Non-Final Office Action", dated Feb. 8, 2017, 25 pages.
U.S. Appl. No. 15/167,512, "Non-Final Office Action", dated Dec. 30, 2016, 21 pages.
U.S. Appl. No. 15/167,512, "Notice of Allowance", dated Jul. 11, 2017, 7 pages.
U.S. Appl. No. 15/167,528, "Final Office Action", dated Mar. 12, 2018, 16 pages.
U.S. Appl. No. 15/167,528, "Final Office Action", dated Jun. 6, 2017, 30 pages.
U.S. Appl. No. 15/167,528, "Non-Final Office Action", dated Nov. 8, 2017, 17 pages.
U.S. Appl. No. 15/167,528, "Non-Final Office Action", dated Jan. 13, 2017, 23 pages.
U.S. Appl. No. 15/167,530, "Non-Final Office Action", dated Nov. 21, 2016, 29 pages.
U.S. Appl. No. 15/167,530, "Notice of Allowance", dated Mar. 24, 2017, 15 pages.
U.S. Appl. No. 15/634,919, "Non-Final Office Action", dated Dec. 28, 2017, 10 pages.
U.S. Appl. No. 15/634,919, "Notice of Allowance", dated Aug. 7, 2018, 5 pages.
CA2,854,084, "Office Action", dated Aug. 29, 2018, 5 pages.
Carver et al., "Bam View: Viewing Mapped Read Alignment Data in the Context of the Reference Sequence", Bioinformatics, vol. 26, No. 5, Jan. 12, 2010, pp. 676-677.
Choi et al., "Genetic diagnosis by whole exome capture and massively parallel DNA sequencing", Proceedings of the National Academy of Science 106.45, 2009, 19096-19101.
CN201180025750, "First Office Action", dated Jul. 14, 2015, 26 pages.
CN201180025750, "Notification to Grant Patent Right for Invention", dated Sep. 26, 2016, 2 pages.
CN201180025750, "Second Office Action", dated Feb. 15, 2016, 24 pages.
CN201180025750, "Third Office Action", dated Jun. 2, 2016, 6 pages.

(56) References Cited

OTHER PUBLICATIONS

CN201180076272, "First Office Action", dated Mar. 30, 2015, 9 pages.
CN201180076272, "Notification to Grant Patent Right", dated Jan. 10, 2017, 2 pages.
CN201180076272, "Second Office Action", dated Dec. 15, 2015, 8 pages.
CN201180076272, "Third Office Action", dated May 25, 2016, 6 pages.
Dean et al., "Genetic restriction of HIV-1 infection and progression to AI OS by a deletion allele of the CKR5 structural gene", Science 273.5283, 1996, 1856-1862.
Edmonson et al., "Bambino: a variant detector and alignment view for next-generation seequencing data in the SAM/BAM format.", Bioinformatics, vol. 27, No. 6, Jan. 28, 2011, pp. 865-866.
EP11875775, "Extended European Search Report", dated Aug. 15, 2015, 13 pages.
EP15159392, "Extended European Search Report", dated Nov. 19, 2015, 12 pages.
EP15159392.8, "Office Action", dated Feb. 5, 2018, 7 pages.
Flicek et al., "Sense from sequence reads: methods for alignment and assembly", Nature Methods Supplement, vol. 6, Issue 11S, 2009, pp. S6-S12.
Giardine et al., "Galaxy: a platform for interactive large-scale genome analysis", Genome research 15.10, 2005, 1451-1455.
Gondro, "A Simple Genetic Algorithm for Multiple Sequence Alignment", Genetics and Molecular Research, vol. 6, No. 4, Oct. 5, 2007, pp. 964-982.
IN9560/DELNP/2012, "First Examination Report", dated Apr. 6, 2018, 6 pages.
JP2013-0512603, "Office Action", dated May 7, 2015.
JP2013512603, "Decision to Grant Patent", dated Sep. 28, 2016.
JP2013512603, "Notification of Reasons of Refusal", dated Mar. 2, 2016.
JP2014542280, "Decision to Grant Patent", dated May 16, 2016.
JP2014542280, "Notification of Reasons for Refusal", dated Dec. 14, 2015.
JP2014542280, "Office Action", dated Mar. 16, 2015.
JP2016116859, "Decision to Grant Patent", dated Nov. 15, 2017.
JP2016116859, "Notifications of Reasons for Refusal", dated May 29, 2017.
JP2016-211297, "Notice of Allowance", dated Jul. 11, 2018, 3 pages.
JP2016-211297, "Notification of Reasons for Refusal", dated Nov. 8, 2017.
Karolchik et al., "The UCSC genome browser", Current protocols in bioinformatics, 2009, 1-4.
KR10-2012-7033515, "Notification of Reasons for Refusal", dated Dec. 20, 2017.
KR10-2012-7033515, "Office Action", dated Aug. 23, 2018, 10 pages.
KR10-2014-7016109, "Decision of Grant", dated Jul. 1, 2016.
KR10-2014-7016109, "Notice of Final Rejection", dated Apr. 27, 2016.
KR10-2014-7016109, "Notification of Reasons for Refusal", dated Mar. 16, 2015.
KR10-2014-7016109, "Notification of Reasons for Refusal", dated Nov. 16, 2014.
KR10-2014-7016109, "Notification of Reasons for Refusal", dated Oct. 13, 2015.
KR10-2015-7001305, "Notification of Reasons for Refusal", dated Feb. 20, 2018.
KR10-2016-7014294, "Notification of Reasons for Refusal", dated Feb. 20, 2018.
Kraus et al., "A position 12-activated H-ras oncogene in all HS578T mammary carcinosarcoma cells but not normal mammary cells of the same patient", Proceedings of the National Academy of Sciences 81.17, 1984, 5384-5388.
Krzywinski et al., "Circos: An Information Aesthetic for Comparative Genomics", Genome Research, vol. 19, No. 9, Jun. 18, 2009, pp. 1639-1645.
Kuhn et al., "The UCSC Genome Browser Database: update 2009", Nucleic Acids Research, vol. 37, Jan. 2009, pp. D755-D761.
Li et al., "Mapping Short DNA Sequencing Reads and Calling Variants Using Mapping Quality Scores", Genome Research, vol. 18, Nov. 2008, pp. 1851-1858.
Li et al., "The Sequence Alignment/Map format and SAM tools", Bioinformatics, vol. 25, 2009, pp. 2078-2079.
Mariadason et al., "Genetic reprogramming in pathways of colonic cell maturation induced by short chain fatty acids: comparison with trichostatin a, sulindac, and curcumin and implications for chemoprevention of colon cancer", Cancer research 60.16, 2000, 4561-4572.
PCT/US2011/000939, "International Preliminary Report on Patentability", dated Nov. 27, 2012, 7 pages.
PCT/US2011/000939, "Written Opinion of the International Searching Authority", dated Nov. 25, 2012, 6 pages.
PCT/US2011/001996, "International Preliminary Report on Patentability", dated May 20, 2014, 5 pages.
PCT/US2011/001996, "International Search Report and Written Opinion", dated Oct. 4, 2012, 7 pages.
Popova et al., "Genome Alteration Print (GAP): a tool to visualize and mine complex cancer genomic profiles obtained by SNP arrays", Genome Biology 2009, 10:R128 (doi: 10.1186/gb-2009-10-11-r128), Nov. 11, 2009, 14 pages.
Quinlan et al., "BEDTools: A Flexible Suite of Utilities for Comparing Genomic Features", Bioinformatics, vol. 26, No. 6, Mar. 15, 2010, pp. 841-842.
Rhead et al., "The UCSC genome browser database: update 201 O", Nucleic acids research 38.suppl 1, 2010, D613-D619.
Robinson et al., "Integrative Genomics Viewer", Nature Biotechnology, vol. 29, No. 1, Jan. 10, 2011, pp. 24-26.
Sanborn, "Tumor versus Matched-Normal Sequencing Analysis and Data Integration", Dissertation. University of California Santa Cruz, Dec. 2012, 156 pages.
Sjöblom et al., "The Consensus Coding Sequences of Human Breast and Colorectal Cancers", Science, vol. 314, No. 5797, Oct. 13, 2006, pp. 268-274.
Stratton et al., "The Cancer Genome", Nature, vol. 458, No. 7239, Apr. 9, 2009, pp. 719-724.
Thompson et al., "A comprehensive comparison of multiple sequence alignment programs", Nucleic Acids Research, vol. 27, No. 13, 1999, 2682-2690.
Wheeler et al., "The Complete Genome of an Individual by Massively Parallel DNA Sequencing", Nature, vol. 452, Apr. 2008, pp. 872-877.
Zhu et al., "Comparative genomics search for losses of long-established genes on the human lineage", PLoS computational biology 3.12, 2007, e247.
U.S. Appl. No. 14/567,774, "Corrected notice of Allowability", dated Feb. 13, 2019, 2 pages.
U.S. Appl. No. 14/567,774, "Corrected Notice of Allowability", dated Jan. 30, 2019, 2 pages.
U.S. Appl. No. 15/167,528, "Corrected Notice of Allowance", dated Feb. 6, 2019, 4 pages.
U.S. Appl. No. 15/167,528, "Corrected Notice of Allowance", dated Feb. 19, 2019, 5 pages.
CA2,797,645, "Office Action", dated Jan. 17, 2019, 5 pages.
U.S. Appl. No. 15/167,528, "Notice of Allowance", dated Nov. 13, 2018, 9 pages.
Daves et al., "Meta-Analysis of Multiple Microarray Datasets Reveals a Common Gene Signature of Metastasis in Solid Tumors", BMC Medical Genomics, vol. 4, No. 56, Jul. 7, 2011, pp. 1-14.
KR10-2015-7001305, "Notice of Decision to Grant", dated Nov. 6, 2018, 2 pages.
KR102913-1097020, "Office Action", dated Sep. 28, 2018, 11 pages.
U.S. Appl. No. 15/476,337, "Notice of Allowability", dated Jun. 18, 2020, 2 pages.
U.S. Appl. No. 15/594,422, "Notice of Allowance", dated Jun. 22, 2020, 8 pages.

(56) References Cited

OTHER PUBLICATIONS

U.S. Appl. No. 15/808,722, "Corrected Notice of Allowability", dated May 28, 2020, 2 pages.
CN201710190109.X, "Office Action", dated May 27, 2020, 21 pages.
JP2019-089447, "Office Action", dated May 21, 2020, 6 pages.
U.S. Appl. No. 15/476,337, "Notice of Allowance", dated Jan. 27, 2020, 9 pages.
U.S. Appl. No. 15/594,422, "Non-Final Office Action", dated Feb. 21, 2020, 10 pages.
Homer et al., "Improved Variant Discovery Through Local Re-Alignment of Short-Read Next-Generation Sequencing Data Using SRMA", Genome Biology, vol. 11, No. 99, 2010, pp. 1-12.
IN3680/DELNP/2014, "First Examination Report", dated Jan. 23, 2020, 8 pages.
KR10-2019-7032370, "Office Action", dated Feb. 6, 2020, 11 pages.
KR10-2019-7032542, "Office Action", dated Feb. 6, 2020, 9 pages.
Meyerson et al., "Advances in Understanding Cancer Genomes through Second-generation Sequencing", Nature Reviews Genetics, vol. 11, Oct. 2010, pp. 685-696.
U.S. Appl. No. 15/618,003, "Notice of Allowance", dated Nov. 12, 2020, 9 pages.
AU2020200022, "First Examination Report", dated Oct. 9, 2020, 5 pages.
KR10-2019-7032542, "Office Action", dated Sep. 25, 2020, 9 pages.
U.S. Appl. No. 15/167,507, "Notice of Allowance", dated Aug. 3, 2020, 11 pages.
U.S. Appl. No. 15/618,003, "Non-Final Office Action", dated Jul. 21, 2020, 16 pages.
U.S. Appl. No. 16/107,862, "Non-Final Office Action", dated Sep. 4, 2020, 22 pages.
EP15159392.8, "Office Action", dated Aug. 13, 2020, 13 pages.
JP2018-151206, "Office Action", dated Jul. 22, 2020, 3 pages.
JP2019-089447, "Notice of Decision to Grant", dated Sep. 14, 2020, 3 pages.
Pham et al., "Synthesis and Biological Evaluation of Novel 2,4-Disubstituted Quinazoline Analogues as GPR119 Agonists", Bioorganic & Medicinal Chemistry, vol. 21, No. 5, Mar. 1, 2013, pp. 1349-1356.
U.S. Appl. No. 15/476,337, "Non-Final Office Action", dated Oct. 2, 2019, 17 pages.
U.S. Appl. No. 15/808,722, "Non-Final Office Action", dated Sep. 6, 2019, 13 pages.
AU2016203450, "Second Examination Report", dated Nov. 8, 2019, 4 pages.
AU2016210784, "Second Examination Report", dated Oct. 30, 2019, 4 pages.
CN201710190109.X, "Office Action", dated Sep. 26, 2019, 19 pages.

* cited by examiner

BAMBAM: PARALLEL COMPARATIVE ANALYSIS OF HIGH-THROUGHPUT SEQUENCING DATA

CROSS-REFERENCE TO RELATED APPLICATIONS

This application is a continuation of U.S. application Ser. No. 15/634,919, filed Jun. 27, 2017, which is a continuation of U.S. application Ser. No. 15/167,530, filed May 27, 2016, which is a continuation of U.S. application Ser. No. 13/134, 047, filed May 25, 2011, which claims the benefit of U.S. Provisional Application No. 61/396,356, filed May 25, 2010, the entire contents of which are hereby incorporated by reference.

BACKGROUND

A central premise in modern cancer treatment is that patient diagnosis, prognosis, risk assessment, and treatment response prediction can be improved by stratification of cancers based on genomic, transcriptional and epigenomic characteristics of the tumor alongside relevant clinical information gathered at the time of diagnosis (for example, patient history, tumor histology and stage) as well as subsequent clinical follow-up data (for example, treatment regimens and disease recurrence events).

With the release of multiple tumor and matched normal whole genome sequences from projects like The Cancer Genome Atlas (TCGA), there is great need for computationally efficient tools that can extract as much genomic information as possible from these enormous datasets (TCGA, 2008). Considering that a single patient's whole genome sequence at high coverage (>30×) can be hundreds of gigabytes in compressed form, an analysis comparing a pair of these large datasets is slow and difficult to manage, but absolutely necessary in order to discover the many genomic changes that occurred in each patient's tumor.

Breast cancer is clinically and genomically heterogeneous and is composed of several pathologically and molecularly distinct subtypes. Patient responses to conventional and targeted therapeutics differ among subtypes motivating the development of marker guided therapeutic strategies. Collections of breast cancer cell lines mirror many of the molecular subtypes and pathways found in tumors, suggesting that treatment of cell lines with candidate therapeutic compounds can guide identification of associations between molecular subtypes, pathways and drug response. In a test of 77 therapeutic compounds, nearly all drugs show differential responses across these cell lines and approximately half show subtype-, pathway and/or genomic aberration-specific responses. These observations suggest mechanisms of response and resistance that may inform clinical drug deployment as well as efforts to combine drugs effectively.

There is currently a need to provide methods that can be used in characterization, diagnosis, treatment, and determining outcome of diseases and disorders.

BRIEF DESCRIPTION OF THE INVENTION

The invention provides methods for generating databases that may be used to determine an individual's risk, in particular, for example, but not limited to, risk of the individual's predisposition to a disease, disorder, or condition; risk at the individual's place of work, abode, at school, or the like; risk of an individual's exposure to toxins, carcinogens, mutagens, and the like, and risk of an individual's dietary habits. In addition, the invention provides methods that may be used for identifying a particular individual, animal, plant, or microorganism.

In one embodiment, the invention provides a method of deriving a differential genetic sequence object, the method comprising: providing access to a genetic database storing (a) a first genetic sequence string representing a first tissue and (b) a second genetic sequence string representing a second tissue, wherein the first and second sequence strings have a plurality of corresponding sub-strings; providing access to a sequence analysis engine coupled with the genetic database; producing, using the sequence analysis engine, a local alignment by incrementally synchronizing the first and second sequence strings using a known position of at least one of plurality of corresponding sub-strings; using, by the sequence analysis engine, the local alignment to generate a local differential string between the first and second sequence strings within the local alignment; and using, by the sequence analysis engine, the local differential string to update a differential genetic sequence object in a differential sequence database. In a preferred embodiment, the first and second genetic sequence strings represent at least 10% of a genome, transcriptome, or proteome of the first and second tissues, respectively. In an alternative preferred embodiment, the first and second genetic sequence strings represent at least 50% of a genome, transcriptome, or proteome of the first and second tissues, respectively. In another alternatively preferred embodiment, the first and second genetic sequence strings represent substantially the entire genome, transcriptome, or proteome of the first and second tissues, respectively. In another preferred embodiment, the corresponding sub-strings comprise homozygous alleles. In an alternative preferred embodiment, the corresponding sub-strings comprise heterozygous alleles. In another more preferred embodiment, the genetic sequence object comprises a file. In a yet more preferred embodiment, the file conforms to a standardized format. In a most preferred embodiment, the file conforms to a SAM/BAM format.

In a preferred embodiment, the step of synchronizing comprises aligning at least one of the plurality of sub-strings is based on an a priori known location within the first string. In an alternative preferred embodiment the step of synchronizing comprises aligning at least one of the plurality of sub-strings based on a known reference string comprising known locations for the at least one of the plurality of sub-strings. In a more preferred embodiment, the known reference string is a consensus sequence.

In another preferred embodiment, the step of synchronizing comprises aligning the at least one of the plurality of sub-strings within a window having a length of less than a length of the at least one of the plurality of sub-strings.

In another preferred embodiment, the differential genetic sequence object represents a plurality of local differential strings for at least one chromosome.

In another preferred embodiment, the differential genetic sequence object represents a plurality of local differential strings for substantially the entire genome of the first tissue.

In a yet other preferred embodiment, the differential genetic sequence object comprises an attribute comprising metadata describing the differential genetic sequence object. In a more preferred embodiment, the attribute comprises a state of at least one of the first and second tissues. In a yet more preferred embodiment, the state comprises a physiological state of at least one of the first and second tissues. In a most preferred embodiment, the physiological state comprises a state selected from the group consisting of neoplastic growth, apoptosis, state of differentiation, tissue age, and responsiveness to treatment.

In an alternative more preferred embodiment, the state comprises genetic status. In a most preferred embodiment, the genetic status comprises a status selected from the group consisting of at least one ploidy, gene copy number, repeat copy number, inversion, deletion, insertion of viral genes, somatic mutation, germline mutation, structural rearrangement, transposition, and loss of heterozygosity.

In an alternative more preferred embodiment, the state comprises pathway model information associated with a signaling pathway within the tissues. In a most preferred embodiment, the signaling pathway is selected from the group consisting of a growth factor signaling pathway, a transcription factor signaling pathway, an apoptosis pathway, a cell cycle pathway, and a hormone response pathway.

In an alternative embodiment, the first and second tissues originate from the same biological entity, the biological entity selected from the group consisting of a patient, a healthy individual, a cell line, a stem cell, an experimental animal model, a recombinant bacterial cell, and a virus. In an alternative embodiment, the first tissue is a healthy tissue and wherein the second is a diseased tissue. In a more preferred embodiment, the diseased tissue comprises a tumor tissue.

The invention also provides the method as disclosed herein, wherein the method further comprises the step of iteratively incrementally synchronizing the first and second sequence strings throughout the entire length of the first sequence string.

The invention also provides a method of providing a health care service, the method comprising: providing access to an analysis engine that is informationally coupled to a medical records storage device, wherein the storage device stores a differential genetic sequence object for a patient; producing, by the analysis engine, a patient-specific data set using presence of a local differential string or constellation of a plurality of local differential strings in the differential genetic sequence object for the patient; and producing, by the analysis engine, a patient-specific instruction based on the patient-specific data set. In a preferred embodiment the medical records storage device is configured as a smart-card and is carried by the patient. In another preferred embodiment, the medical records storage device is remotely accessible by a healthcare provider. In a yet other preferred embodiment, the differential genetic sequence object for the patient comprises a plurality of local differential strings for at least two chromosomes. In a still further preferred embodiment, the differential genetic sequence object for the patient comprises a plurality of local differential strings for substantially the entire genome of the patient. In another preferred embodiment, the differential genetic sequence object for the patient comprises a plurality of local differential strings representing at least two tissue types, or at least two temporally spaced results for the same tissue. In a more preferred embodiment, the at least two temporally spaced results for the same tissue are obtained from before and after commencement of a treatment. In a most preferred embodiment, the at least two temporally spaced results for the same tissue are obtained from before and after commencement of a treatment.

In another alternative preferred embodiment, the patient-specific instruction as disclosed herein is selected from the group consisting of a diagnosis, a prognosis, a prediction of treatment outcome, a recommendation for a treatment strategy, and a prescription.

The invention also provides a method of analyzing a population, the method comprising: obtaining and storing a plurality of differential genetic sequence objects in a medical records database of a population, wherein the records database is informationally coupled to an analysis engine; identifying, by the analysis engine, a constellation of a plurality of local differential strings within the plurality of differential genetic sequence objects to produce a constellation record; and using, by the analysis engine, the constellation record to generate a population analysis record. In a preferred embodiment, the population comprises a plurality of blood relatives. In an alternative preferred embodiment, the population comprises a plurality of members characterized by sharing at least one common feature selected from the group consisting of exposure to a pathogen, exposure to a noxious agent, health history, treatment history, treatment success, gender, species, and age. In another alternatively preferred embodiment, the population comprises a plurality of members characterized by sharing at least one common feature selected from the group consisting of geographic location, ethnicity, and occupation. In a still further alternatively preferred embodiment, the population analysis record comprises paternity or maternity confirmation.

In an alternative embodiment the method disclosed herein further comprises a step of comparing a constellation record of an individual patient with the population analysis record. In a preferred embodiment, the step of comparing of the constellation record of the individual patient with the population analysis record creates a patient-specific record. In a more preferred embodiment, the patient-specific record comprises a risk assessment or an identification of the patient as belonging to a specified population. In an alternative more preferred embodiment, the patient-specific record comprises a diagnosis, a prognosis, a prediction of treatment outcome, a recommendation for a treatment strategy, and a prescription.

The invention further provides a method of analyzing a differential genetic sequence object of a person, the method comprising: storing a reference differential genetic sequence object in a medical records database that is informationally coupled to an analysis engine; calculating, by the analysis engine, a deviation between a plurality of local differential strings in the differential genetic sequence object of the person and a plurality of local differential strings in the reference differential genetic sequence object to produce a deviation record; using, by the analysis engine, the deviation record to generate a person-specific deviation profile. In a preferred embodiment, the reference differential genetic sequence object is calculated from a plurality of local differential strings of the person. In another preferred embodiment, the reference differential genetic sequence object is calculated from a plurality of local differential strings of the person.

With respect to the various methods disclosed herein, in a preferred embodiment the patient or person is selected from the group consisting of a patient or person diagnosed with a condition, the condition selected from the group consisting of a disease and a disorder. In a more preferred embodiment, the condition is selected from the group consisting of acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Hunington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In another preferred embodiment, the condition is selected from the group consisting of cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system.

In a still further alternative preferred embodiment, the condition is selected from the group consisting of endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

The invention further provides a method of deriving a differential genetic sequence object, the method comprising: providing access to a genetic database storing (a) a first genetic sequence string representing a first tissue and (b) a second genetic sequence string representing a second tissue, wherein the first and second sequence strings have a plurality of corresponding sub-strings; providing access to a sequence analysis engine coupled with the genetic database; using the sequence analysis engine to produce a local alignment by incrementally synchronizing the first and second sequence strings using a known position of at least one of plurality of corresponding sub-strings; using, by the sequence analysis engine, the local alignment to generate a local differential string between the first and second sequence strings within the local alignment; and using, by the sequence analysis engine, the local differential string to create a differential genetic sequence object in a differential sequence database, thereby deriving a differential sequence object.

The invention further provides a transformation method for creating a differential genetic sequence object, the differential genetic sequence object representing a clinically-relevant difference between a first genetic sequence and a second sequence, the method comprising the steps of: (i) providing access to a genetic database storing (a) a first genetic sequence string representing a first tissue and (b) a second genetic sequence string representing a second tissue, wherein the first and second sequence strings have a plurality of corresponding sub-strings; (ii) providing access to a sequence analysis engine coupled with the genetic database; (iii) using the sequence analysis engine to produce a local alignment by incrementally synchronizing the first and second sequence strings using a known position of at least one of plurality of corresponding sub-strings; (iv) using, by the sequence analysis engine, the local alignment to generate a local differential string between the first and second sequence strings within the local alignment; and (v) using, by the sequence analysis engine, the local differential string to create a differential genetic sequence object in a differential sequence database, thereby deriving a differential sequence object, wherein the differential sequence object provides objective information to a user.

In a preferred embodiment, the objective information is selected from the group consisting of, genetically relevant information, metabolically relevant information, toxicologically relevant information, clinically relevant information, temporally relevant information, geographically relevant information, occupational risk relevant information, life history relevant information, and the like.

DETAILED DESCRIPTION OF THE INVENTION

Figure 1:
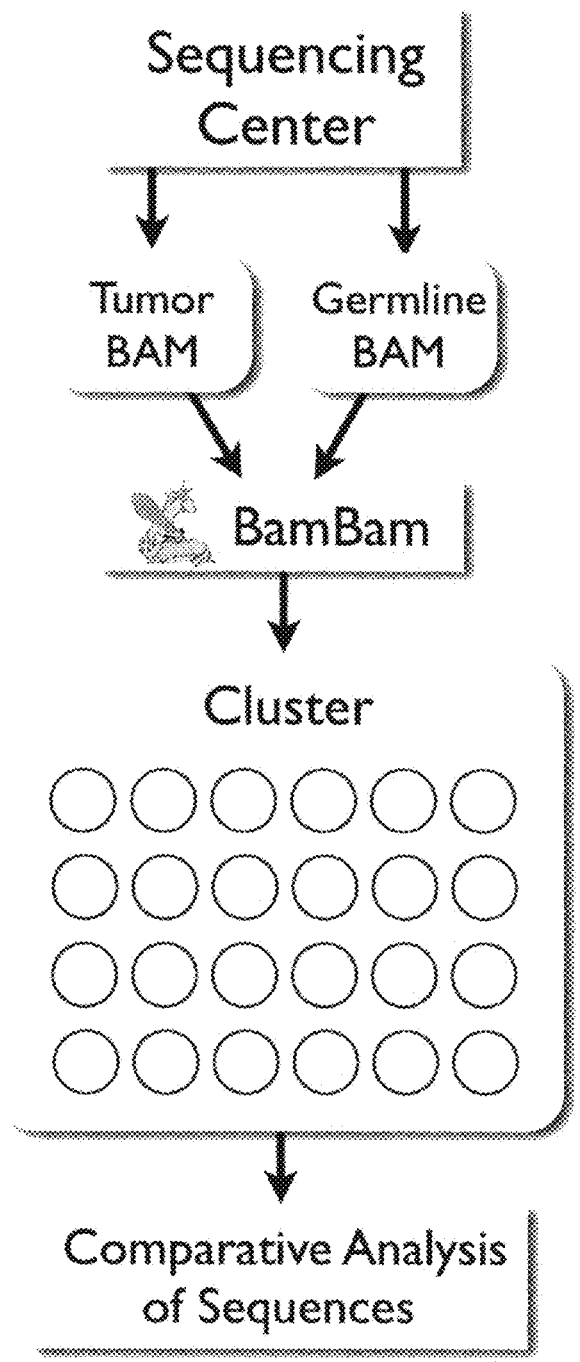
FIG. 1 illustrates a schematic of "BamBam" data flow.

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "an allele" includes a plurality of such alelles, and a reference to "a cluster" is a reference to one or more clusters and equivalents thereof, and so forth.

As used herein, the term "curated" means the relationships between a set of biological molecules and/or non-biological molecules that has been tested, analyzed, and identified according to scientific and/or clinical principles using methods well known in the art, such as molecular biological, biochemical, physiological, anatomical, genomic, transcriptomic, proteomic, metabolomic, ADME, and bioinformatic techniques, and the like. The relationships may be biochemical such as biochemical pathways, genetic pathways, metabolic pathways, gene regulatory pathways, gene transcription pathways, gene translation pathways, miRNA-regulated pathways, pseudogene-regulated pathways, and the like.

High-throughput data is providing a comprehensive view of the molecular changes in cancer tissues. New technologies allow for the simultaneous genome-wide assay of the state of genome copy number variation, gene expression, DNA methylation, and epigenetics of tumor samples and cancer cell lines.

Studies such as The Cancer Genome Atlas (TCGA), Stand Up To Cancer (SU2C), and many more are planned in the near future for a wide variety of tumors. Analyses of current data sets find that genetic alterations between patients can differ but often involve common pathways. It is therefore critical to identify relevant pathways involved in cancer progression and detect how they are altered in different patients.

With the release of multiple fully-sequenced tumor and matched normal genomes from projects like The Cancer Genome Atlas (TCGA), there is great need for tools that can efficiently analyze these enormous datasets.

To this end, we developed BamBam, a tool that simultaneously analyzes each genomic position from a patient's tumor and germline genomes using the aligned short-read data contained in SAM/BAM-formatted files (SAMtools library; Li H, Handsaker B, Wysoker A, Fennell T, Ruan J, Homer N, Marth G, Abecasis G, Durbin R; 1000 Genome Project Data Processing Subgroup. The Sequence Alignment/Map format and SAMtools. *Bioinformatics*. 2009 Aug. 15; 25(16):2078-9. Epub 2009 Jun. 8). BamBam interfaces with the SAMtools library to simultaneously analyze a patient's tumor and germline genomes using short-read alignments from SAM/BAM-formatted files. In the present disclosure the BamBam tool can be a sequence analysis engine that is used to compare sequences, the sequences comprising strings of information. In one embodiment, the strings of information comprise biological information, for example, a polynucleotide sequence or a polypetide sequence. In another embodiment, the biological information can comprise expression data, for example relative concentration levels of mRNA transcripts or rRNA or tRNA or peptide or polypeptide or protein. In another embodiment, the biological information can be relative amounts of protein modification, such as for example, but not limited to, phosphorylation, sulphation, actylation, methylation, glycosilation, sialation, modification with glycosylphosphatidylinositol, or modification with proteoglycan.

This method of processing enables BamBam to efficiently calculate overall copy number and infer regions of structural variation (for example, chromosomal translocations) in both tumor and germline genomes; to efficiently calculate overall and allele-specific copy number; infer regions exhibiting loss of heterozygosity (LOH); and discover both somatic and germline sequence variants (for example, point mutations) and structural rearrangements (for example, chromosomal fusions. Furthermore, by comparing the two genome sequences at the same time, BamBam can also immediately distinguish somatic from germline sequence variants, calculate allele-specific copy number alterations in the tumor genome, and phase germline haplotypes across chromosomal regions where the allelic proportion has shifted in the tumor genome. By bringing together all of these analyses into a single tool, researchers can use BamBam to discover many types of genomic alterations that occurred within a patient's tumor genome, often to specific gene alleles, that help to identify potential drivers of tumorigenesis.

To determine if a variant discovered is somatic (that is, a variant sequence found only in the tumor) or a germline (that is, a variant sequence that is inherited or heritable) variant requires that we compare the tumor and matched normal genomes in some way. This can be done sequentially, by summarizing data at every genomic position for both tumor and germline and then combining the results for analysis. Unfortunately, because whole-genome BAM files are hundreds of gigabytes in their compressed form (1-2 terabytes uncompressed), the intermediate results that would need to be stored for later analysis will be extremely large and slow to merge and analyze.

To avoid this issue, BamBam reads from two files at the same time, constantly keeping each BAM file in synchrony with the other and piling up the genomic reads that overlap every common genomic location between the two files. For each pair of pileups, BamBam runs a series of analyses listed above before discarding the pileups and moving to the next common genomic location. By processing these massive BAM files with this method, the computer's RANI usage is minimal and processing speed is limited primarily by the speed that the filesystem can read the two files. This enables BamBam to process massive amounts of data quickly, while being flexible enough to run on a single computer or across a computer cluster. Another important benefit to processing these files with BamBam is that its output is fairly minimal, consisting only of the important differences found in each file. This produces what is essentially a whole-genome diff between the patient's tumor and germline genomes, requiring much less disk storage than it would take if all genome information was stored for each file separately.

BamBam is a computationally efficient method for surveying large sequencing datasets to produce a set of high-quality genomic events that occur within each tumor relative to its germline. These results provide a glimpse into the chromosomal dynamics of tumors, improving our understanding of tumors' final states and the events that led to them. An exemplary scheme of BamBam Data Flow is shown at FIG. 1.

One particular exemplary embodiment of the invention is creation and use of a differential genetic sequence object. As used herein, the object represents a digital object instantiated from the BamBam techniques and reflects a difference between a reference sequence (for example, a first sequence) and an analysis sequence (for example, a second sequence). The object may be considered a choke point on many different markets. One might consider the following factors related to use and management of such objects from a market perspective:

An object can be dynamic and change with respect to a vector of parameters (for example, time, geographic region, genetic tree, species, etc.)

Objects can be considered to have a "distance" relative to each other objects or reference sequences. The distance can be measured according to dimensions of relevance. For example, the distance can be a deviation from a hypothetical normal or a drift with respect to time.

Objects can be indicative of risk: risk of developing disease, susceptibility to exposure, risk to work at a location, etc.

Objects can be managed for presentation to stakeholders: health care providers, insurers, patients, etc.
  Can be presented as a graphical object
  Can be presented in a statistical format: single person, a population, a canonical human, etc.

A reference sequence can be generated from the objects to form a normalized sequence. The normalized sequence can be built based on consensus derived from measured objects.

Objects are representative of large sub-genomic or genomic information rather than single-gene alignments and are annotated/contain meta data readable by standard software.

Objects can have internal patterns or structures which can be detected: a set of mutations in one spot might correlate to a second set of mutations in another spot which correlates to a condition; constellation of difference patterns could be a hot spot; use multi-variate analysis or other AI techniques to identify correlations; detect significance of a hot spot (for example, presence, absence, etc.)

Objects related to a single person could be used as a security key

Updating a differential sequence object: Update includes creating, modifying, changing, deleting, etc.;
  Can be based on a template
  Can be a de novo object
  Can be an existing object In an alternative exemplary embodiment the method can be used to acertain and predict responsiveness of a patient to treatment: anticipated, assumed, predicted, actual, and the like.

In an alternative exemplary embodiment the method can be used to provide patient-specific instructions: prescription, recommendation, prognosis, and the like.

In one embodiment, the method may be used to provide clinical information that can be used in a variety of diagnostic and therapeutic applications, such as detection of cancer tissue, staging of cancer tissue, detection of metastatic tissue, and the like; detection of neurological disorders, such as, but not limited to, Alzheimer's disease, amyotrophic lateral sclerosis (ALS), Parkinson's disease, schizophrenia, epilepsy, and their complications; developmental disorders such as DiGeorge Syndrome, autism, autoimmune disorders such as multiple sclerosis, diabetes, and the like; treatment of an infection, such as, but not limited to, viral infection, bacterial infection, fungal infection, leishmania, schistosomiasis, malaria, tape-worm, elephantiasis, infections by nematodes, nematines, and the like.

In one embodiment, the method may be used to provide clinical information to detect and quantify altered gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, for a condition associated with altered expression of a gene or protein. Conditions, diseases or disorders associated with altered expression include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

In another embodiment, the method may be used to provide clinical information to detect and quantify altered gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, for a disorder associated with altered expression of a gene or protein. Disorders associated with altered expression include akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In one embodiment, the method may be used to provide clinical information for a condition associated with altered expression or activity of the mammalian protein. Examples of such conditions include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In yet another embodiment, the method may be used to provide clinical information to detect and quantify altered gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, for a disorder associated with altered expression of a gene or protein. Examples of such disorders include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina *bifida*, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system.

In another embodiment, the method may be used to provide clinical information to detect and quantify altered gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, for a disorder associated with altered expression of a gene or protein. Examples of such a disorder include, but are not limited to, endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences may be used in Southern or Northern analysis, dot blot, or other membrane-based technologies; in PCR technologies; in dipstick, pin, and ELISA assays; and in microarrays utilizing fluids or tissues from patients to detect altered nucleic acid sequence expression. Such qualitative or quantitative methods are well known in the art.

Characterization and Best Mode of the Invention

"BamBam" is a computationally efficient method for surveying large sequencing datasets to produce a set of high-quality genomic events that occur within each tumor relative to its germline. These results provide a glimpse into the chromosomal dynamics of tumors, improving our understanding of tumors' final states and the events that led to them.

Diagnostics

The methods herein described may be used to detect and quantify altered gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, for a condition, disease, or disorder associated with altered expression of a gene or protein, The methods herein described may be also used to detect and quantify altered gene expression, absence/presence versus excess, expression of mRNAs or to monitor mRNA levels during therapeutic intervention. Conditions, diseases or disorders associated with altered expression include idiopathic pulmonary arterial hypertension, secondary pulmonary hypertension, a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis; acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In another aspect, the nucleic acid of the invention.

The methods described herein may be used to detect and quantify altered gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, for a disorder associated with altered expression of a gene or protein. The methods described herein may be also used to detect and quantify altered gene expression; absence, presence, or excess expression of mRNAs; or to monitor mRNA levels during therapeutic intervention Disorders associated with altered expression include akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate the level that is observed in a normal subject. The assays may also be used to detect, quantify, or measure gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, that indicate and/or identify the presence of a tumor, absence of a tumor, or remission status of the individual undergoing a clinical treatment or therapy. The results obtained from successive assays may be used to show the efficacy of treatment over a period ranging from several days to months.

The methods disclosed herein may also be used to detect, quantify, and correlate a change in gene structures, gene mutations, gene biochemical modifications, including alterations and/or modifications to messenger RNA (mRNA), ribosomal RNA (rRNA), transfer RNA (tRNA), microRNA (miRNA), antisense RNA (asRNA), and the like, that has not been previously identified or associated with a particular clinical disease, disorder, or condition. In the alternative, the methods disclosed herein may be used to identify a novel clinical disease, disorder, or condition. Novel changes in gene structures, gene mutations, and gene biochemical modifications, may then be compared with known chemical and biochemical properties of a nucleic acid sequence or protein sequence and which correlate with a clinical disease, disorder, or condition may be used to generate new databases and knowledge about cellular metabolism for clinical use.

Model Systems

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations. Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle that produces the number of organisms needed to satisfy statistical requirements.

Acute toxicity tests are based on a single administration of the agent to the subject to determine the symptomology or lethality of the agent. Three experiments are conducted: (a) an initial dose-range-finding experiment, (b) an experiment to narrow the range of effective doses, and (c) a final experiment for establishing the dose-response curve.

Prolonged toxicity tests are based on the repeated administration of the agent. Rats and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. Nos. 4,736,866; 5,175,383; and 5,767,337; incorporated herein by reference.) In some cases, the introduced gene may be activated at a specific time in a specific tissue type during fetal development or postnatally. Expression of the transgene is monitored by analysis of phenotype or tissue-specific mRNA expression in transgenic animals before, during, and after challenge with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene that disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Transformed ES cells are identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168: 342-357; Wiles and Keller (1991) Development 111: 259-267; and Klug et al. (1996) J. Clin. Invest. 98: 216-224). Recent developments demonstrate that ES cells derived from human blastocysts may also be manipulated in vitro to differentiate into eight separate cell lineages, including endoderm, mesoderm, and ectodermnal cell types (Thomson (1998) Science 282: 1145-1147).

Knockout Analysis

In gene knockout analysis, a region of a human disease gene candidate is enzymatically modified to include a non-mammalian gene such as the neomycin phosphotransferase gene (neo; see, for example, Capecchi (1989) Science 244: 1288-1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells that contain the integrated human gene are handled as described above. Inbred animals are studied and treated to obtain information on the analogous human condition. These methods have been used to model several human diseases. (See, for example, Lee et al. (1998) Proc. Natl. Acad. Sci. 95: 11371-11376; Baudoin et al. (1998) Genes Dev. 12: 1202-1216; and Zhuang et al. (1998) Mol. Cell Biol. 18: 3340-3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulata*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as "extensive metabolizers" and "poor metabolizers" of these agents.

Exemplary Uses of the Invention

Personalized medicine promises to deliver specific treatment(s) to those patients mostly likely to benefit. We have shown that approximately half of therapeutic compounds are preferentially effective in one or more of the clinically-relevant transcriptional or genomic breast cancer subtypes. These findings support the importance of defining response-related molecular subtypes in breast cancer treatment. We also show that pathway integration of the transcriptional and genomic data on the cell lines reveals subnetworks that provide mechanistic explanations for the observed subtype specific responses. Comparative analysis of subnet activities between cell lines and tumors shows that the majority of subtype-specific subnetworks are conserved between cell lines and tumors. These analyses support the idea that preclinical screening of experimental compounds in a well-characterized cell line panel can identify candidate response-associated molecular signatures that can be used for sensitivity enrichment in early-phase clinical trials. We suggest that this in vitro assessment approach will increase the likelihood that responsive tumor subtypes will be identified before a compound's clinical development begins, thereby reducing cost, increasing the probability of eventual FDA approval and possibly avoiding toxicity associated with treating patients unlikely to respond. In this study we have assessed only molecular signatures that define transcriptional subtypes and selected recurrent genome copy number abnormalities (CNAs). We anticipate that the power and precision of this approach will increase as additional molecular features such as genetic mutation, methylation and alternative splicing, are included in the analysis. Likewise, increasing the size of the cell line panel will increase the power to assess less common molecular patterns within the panel and increase the probability of representing a more complete range of the diversity that exists in human breast cancers.

Here, we disclose a new software tool we have called BamBam that enables a rapid comparison of tumor (somatic) and germline matched sequencing datasets. The results output by BamBam are varied, producing an exhaustive catalogue of the somatic and germline variants contained by each patient's samples. This catalogue provides researchers with the ability to quickly find important changes that occurred during the tumor's development, but also provide high-quality variants present in the patient's germline that may indicate predisposition to disease. Further improvements of BamBam will consist of methods that specifically search for multiple types of variants occurring in the same genomic region (for example, one allele of a gene deleted, the other allele containing a truncating mutation by breakpoint) that may point to drivers of tumorigenesis. We also plan to extend BamBam's ability to processing more than pairs of genomes, as well as provide researchers with the ability to plug in their own analysis methods into BamBam's pipeline.

In additional embodiments, the polynucleotide nucleic acids may be used in any molecular biology techniques that have yet to be developed, provided the new techniques rely on properties of nucleic acid molecules that are currently known, including, but not limited to, such properties as the triplet genetic code and specific base pair interactions.

The invention will be more readily understood by reference to the following examples, which are included merely for purposes of illustration of certain aspects and embodiments of the present invention and not as limitations.

EXAMPLES

Example I: Dataset Synchronization Via the Reference Genome

All short reads are aligned to the same reference genome, making the reference genome a natural way of organizing sequence data from multiple, related samples. BamBam takes in two short read sequencing datasets, one from the tumor and the other a matched normal ("germline") from the same patient, and the reference genome, and reads these datasets such that all sequences in both datasets overlapping the same genomic position are available to be processed at the same time. This is the most efficient method for processing such data, while also enabling complex analyses that would be difficult or impossible to accomplish in a serialized manner, where each dataset is processed by itself, and results are only merged afterwards.

Such a method is easily extendible to more than two related sequencing datasets. For example, if three samples, matched normal, tumor, and relapse, were sequenced, this method could be used to search for changes specific to the tumor & the relapse sample, and changes specific only to the relapse, suggesting the relapse tumor has changed somewhat from the original tumor from which it had presumably derived. Also, one could use this same method to determine the inherited portions of a child's genome given sequenced samples from child, father, and mother.

Example II: Somatic and Germline Variant Calling

Because BamBam keeps the sequence data in the pair of files in sync across the genome, a complex mutation model that requires sequencing data from both tumor and germline BAM files as well as the human reference can be implemented easily. This model aims to maximize the joint probability of both the germline genotype (given the germline reads and the reference nucleotide) and the genotype of the tumor (given the germline genotype, a simple mutation model, an estimate of the fraction of contaminating normal tissue in the tumor sample, and the tumor sequence data).

To find the optimal tumor and germline genotype, we aim to maximize the likelihood defined by $$P(D_g,D_t,G_g,G_t|\alpha r)=P(D_g|G_g)P(G_g|r)P(D_t|G_g,G_t,\alpha)P(G_t|G_g) \quad (1)$$

$P(D_g,D_t,G_g,G_t|\alpha r)=P(D_g|G_g)P(G_g|r)P(D_t|G_g,G_t,\alpha)P(G_t|G_g)$ (1) where r is the observed reference allele, $\alpha$ the fraction of normal contamination, and the tumor and germline genotypes are defined by $G_t=(t_1, t_2)$ and $G_g=(g_1, g_2)$ where $t_1$, $t_2$, $g_1$, $g_2 \in (A, T, C, G)$ The tumor and germline sequence data are defined as a set of reads $D_t=(d_t^1, d_t^2, \ldots, d_t^m)$ and $D_g=(d_g^1, d_g^2, \ldots, d_g^m)$, respectively, with the observed bases $d_t^1, d_g^1 \in (A, T, C, G)$. All data used in the model must exceed user-defined base and mapping quality thresholds.

The probability of the germline alleles given the germline genotype is modeled as a multinomial over the four nucleotides:

$$P(D_g \mid G_g) = \frac{n!}{n_A!n_T!n_G!n_C!}\prod_i^n P(d_g^i \mid G_g),$$

where n is the total number of germline reads at this position and $n_A$, $n_G$, $n_C$, $n_T$ are the reads supporting each observed allele. The base probabilities, $P(D_g|G_g)$, are assumed to be independent, coming from either of the two parental alleles represented by the genotype $G_g$, while also incorporating the approximate base error rate of the sequencer. The prior on the germline genotype is conditioned on the reference base as $$P(G_g|r=a)=\{\mu_{aa},\mu_{ab},\mu_{bb}\},$$

where $\mu_{aa}$ is the probability that the position is homozygous reference, $\mu_{ab}$ is heterozygous reference, and $\mu_{bb}$ is homozygous non-reference. At this time, the germline prior does not incorporate any information on known, inherited SNPs.

The probability of the set of tumor reads is again defined as multinomial $$P(D_t \mid G_t, G_g, \alpha) = \frac{n!}{n_A!n_T!n_G!n_C!}\prod_i^n P(d_t^i \mid G_t, G_g, \alpha),$$

where m is the total number of germline reads at this position and $m_A$, $m_G$, $m_C$, $m_T$ are the reads supporting each observed allele in the tumor dataset, and the probability of each tumor read is a mixture of base probabilities derived from both tumor and germline genotypes that is controlled by the fraction of normal contamination, α, as $$P(d_t^i | G_t, G_g, \alpha) = \alpha P(d_t^i | G_t) + (1-\alpha) P(d_t^i | G_g)$$

and the probability of the tumor genotype is defined by a simple mutation model from on the germline genotype $$P(G_t | G_g) = \max[P(t_1|g_1)P(t_2|g_2), P(t_1|g_2)P(t_2|g_1)],$$

where the probability of no mutation (for example, $t_1 = g_1$) is maximal and the probability of transitions (that is, A→G, T→C) are four times more likely than transversions (that is, A→T,T→G). All model parameters, α, $\mu_{aa}$, $\mu_{ab}$, $\mu_{bb}$, and base probabilities, $P(d^i|G)$, for the multinomial distributions are user-definable.

The tumor and germline genotypes, $G_t^{max}$, $G_g^{max}$, selected are those that maximize (1), and the posterior probability defined by $$\frac{P(D_g, D_t, G_g^{max}, G_t^{max} | \alpha, r)}{\sum_{i,j} P(D_g, D_t, G_g = i, G_t = j | \alpha, r)}$$

can be used to score the confidence in the pair of inferred genotypes. If the tumor and germline genotypes differ, the putative somatic mutation(s) will be reported along with its respective confidence.

Maximizing the joint likelihood of both tumor and germline genotypes helps to improve the accuracy of both inferred genotypes, especially in situations where one or both sequence datasets have low coverage of a particular genomic position. Other mutation calling algorithms, such as MAQ and SNVMix, that analyze a single sequencing dataset are more likely to make mistakes when the non-reference or mutant alleles have low support (Li, H., et al. (2008) Mapping short DNA sequencing reads and calling variants using mapping quality scores, Genome Research, 11, 1851-1858; Goya, R. et al. (2010) SNVMix: predicting single nucleotide variants from next-generation sequencing of tumors, Bioinformatics, 26, 730-736).

In addition to collecting allele support from all reads at a given genomic position, information on the reads are collected (such as which strand, forward or reverse, the read maps to, the position of the allele within the read, the average quality of the alleles, etc.) and used to selectively filter out false positive calls. We expect a random distribution of strands and allele positions for all of the allele supporting a variant, and if the distribution is skewed significantly from this random distribution (that is, all variant alleles are found near the tail end of a read), then this suggest that the variant call is suspect.

Example III: Overall and Allele-Specific Copy Number

Overall somatic copy number is calculated using a dynamic windowing approach that expands and contracts the window's genomic width according to the coverage in either the tumor or germline data. The process is initialized with a window of zero width. Each unique read from either the tumor or germline sequence data will be tallied into tumor counts, Nt, or germline counts, Ng. The start and stop positions of each read will define the window's region, expanding as new reads exceed the boundaries of the current window. When either the tumor or germline counts exceed a user-defined threshold, the window's size and location are recorded, as well as the Nt, Ng, and relative coverage Nt. Tailoring the size of the Ng window according to the local read coverage will create large windows in regions of low coverage (for example, repetitive regions) or small windows in regions exhibiting somatic amplification, thereby increasing the genomic resolution of amplicons and increasing our ability to define the boundaries of the amplification.

Figure 2:
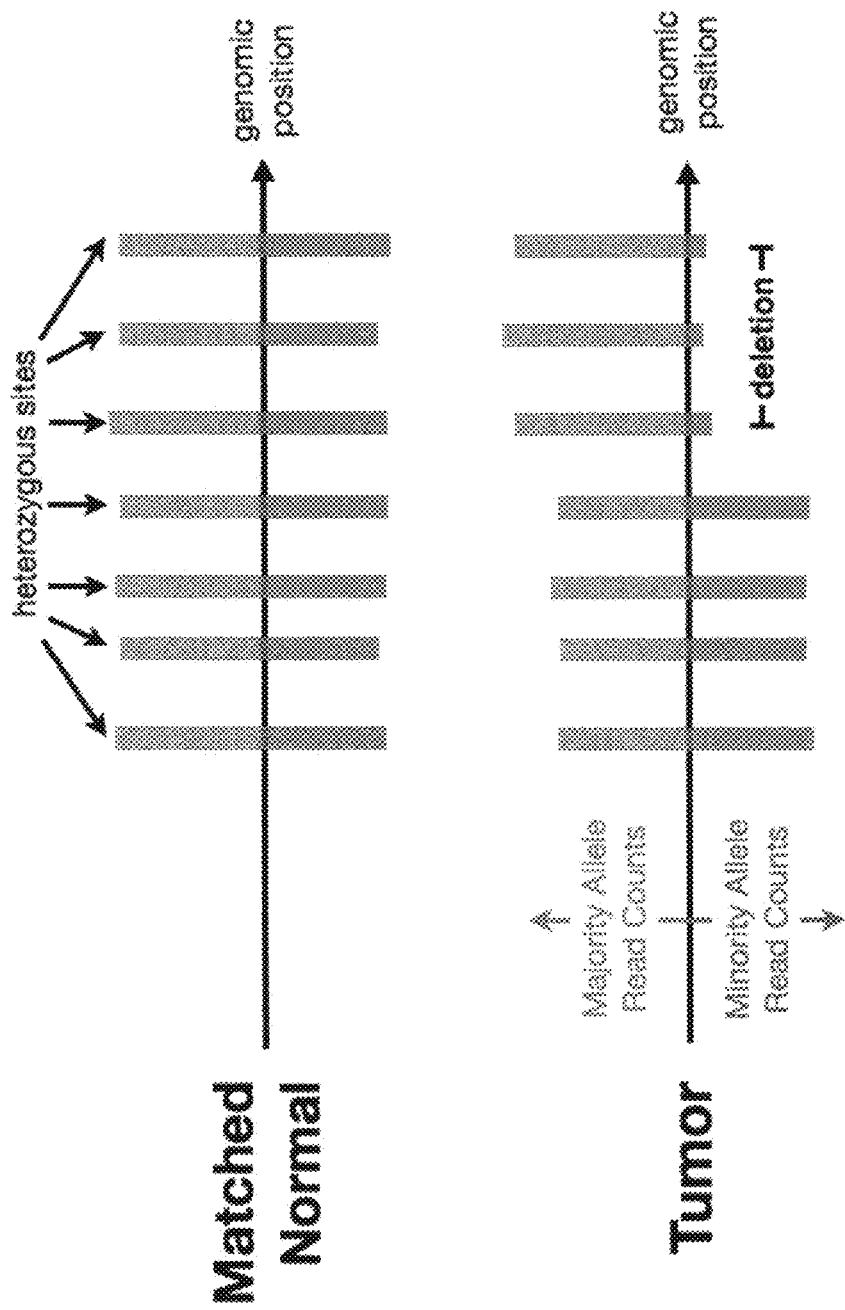
FIG. 2 illustrates an overview of allele-specific copy number calculation.

Allele-specific copy number is calculated similarly, except that only positions deemed heterozygous in the germline are included, as shown (see FIG. 2). Heterozygosity is defined as a position in the germline that is believed to have two different alleles, one allele contributed by each parent. Majority and minority copy numbers are calculated using the same dynamic windowing technique described above for overall copy number in order to aggregate data in the same genomic neighborhood. The majority allele at a heterozygous site is defined herein as the allele that has the greatest number of supporting reads in the tumor dataset that overlap that genomic location, while the minority allele is allele that has the least support. All counts ascribed to the majority allele in both tumor and germline data will go towards calculation of the majority copy number, and similarly for the minority allele. The majority and minority allele counts are then normalized by the counts of both alleles in the germline data, Ng, to calculate majority and minority copy numbers.

Allele-specific copy number is used to identify genomic regions exhibiting loss-of-heterozygosity (both copy-neutral and copy-loss) as well as amplifications or deletions specific to a single allele. This last point is especially important to help distinguish potentially disease-causing alleles as those that are either amplified or not-deleted in the tumor sequence data. Furthermore, regions that experience hemizygous loss (for example, one parental chromosome arm) can be used to directly estimate the amount of normal contaminant in the sequenced tumor sample, which can be used to improve the modeling of the germline and tumor genotypes described above.

FIG. 2 shows an overview of allele-specific copy number calculation. Positions with heterozygous genotypes are determined using both germline and tumor sequencing data, as determined by the germline variant calling algorithm. All reads overlapping these locations are collected and the read support for each of the two alleles in the heterozygous genotype are found in both tumor and germline. The majority allele is determined to be the allele with the highest support, and majority copy number is calculated by normalizing this count by the overall number of reads at that position in the germline.

Example IV: Phasing Genotypes

BamBam attempts to phase all heterozygous positions found in the germline by taking advantage of allelic imbalance caused by large scale genomic amplifications or deletions in the tumor. The majority vote base call is selected at every position in the tumor sequence data to construct the phased haplotype present in the tumor. The majority vote chooses the most abundant allele observed in the pool of short reads, which should select the allele that remains in the tumor after a deletion event or the duplicated allele of an amplification event. At each position, the allelic state of the germline is also identified, where a position is deemed homozygous if there exists only one allele with the requisite read support and heterozygous if at least two alleles have the required read support. The tumor's haplotype is assumed to represent one of the two parental haplotypes, where the second parental haplotype is derived as the sequence of germline alleles that do not belong to the tumor haplotype. This procedure is used genome-wide regardless of the allelic proportion in the tumor, so we expect the haplotype assignment of genotypes to be essentially random in regions that are equally balanced between major and minor alleles. Accurate phasing of germline sequence will only occur in regions that exhibit a consistent allelic imbalance resulting from a single genomic event (for example regional amplification or deletion) in the tumor. Validation of the tumor-derived haplotypes can be accomplished by comparing the tumor-derived haplotypes to phased genotypes available from the HapMap project (International HapMap Consortium (2007), Nature, 7164: 851-861).

Example V: Inferring Structural Variation Using Paired-End Clustering

To identify putative intra- and inter-chromosomal rearrangements, BamBam searches for discordant paired reads where each read in the pair map to disparate regions of the reference sequence. Intra-chromosomal discordant pairs are those that have an abnormally large insert size (i.e. the genomic distance on the reference separating the paired reads exceeds a user-defined threshold) or those that map in an incorrect orientation (i.e. inversion). Inter-chromosomal discordant pairs are defined by paired reads that map to different chromosomes. All discordant paired-end reads that align to identical locations as other pairs are removed to avoid calling rearrangements supported by a large number of reads that are merely the result of the PCR amplification step in the short-read library's preparation. An overview of this process is shown in FIG. 3.

All discordant paired-end reads are clustered according to their genomic locations to define an approximate genomic region where the breakpoint is believed to be. The aggregation process consists of grouping together the unique reads that overlap other reads on both sides of the putative breakpoint. The strand orientation of all overlapping reads must also match or are not include in the cluster of pairs. When the number of overlapping discordant pairs in a cluster exceeds a user-defined threshold, the breakpoint that describes the rearrangement is defined. If there are rearrangements present in both germline and tumor datasets at the same position, then they are compared as follows. Germline rearrangements require that the tumor and germline dataset support the same rearrangement since it is exceedingly unlikely that a structural variation observed in the germline would somehow be reversed in the tumor to precisely agree with the reference. On the other hand, somatic rearrangements must only be observed in the tumor sequencing data, and not substantially present in the germline dataset. Rearrangements that fulfill these requirements are stored for post-processing analysis and visualization, while those that do not are discarded as artifactual rearrangements caused by either the sequencing instrument, sample preparation (such as whole-genome amplification), or a systematic bias of the short-read mapping algorithm employed.

Figure 3:
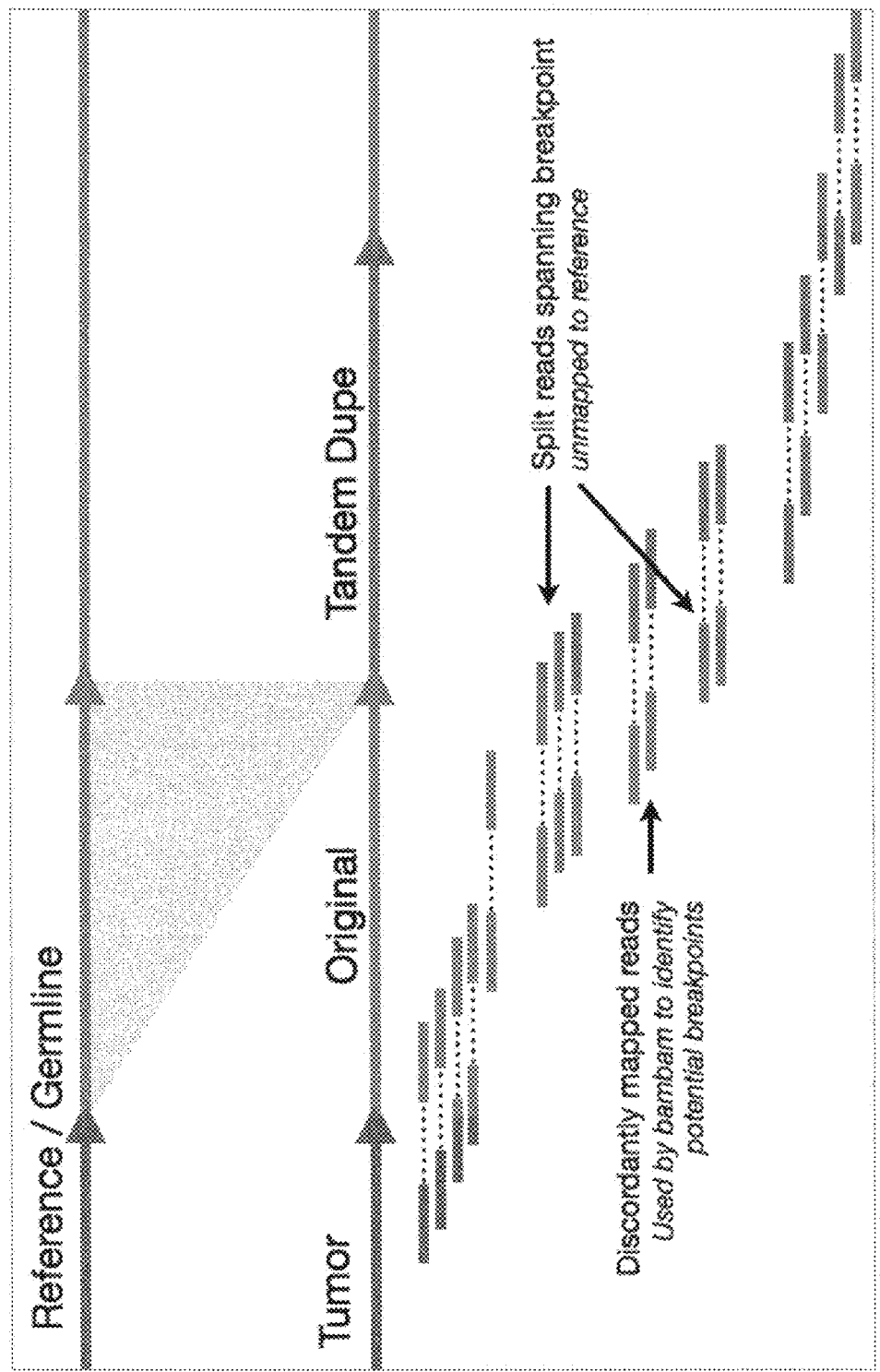
FIG. 3 illustrates an overview of structural variation calling.

FIG. 3 shows an overview of structural variation calling. The initial identification of a putative structural variant is identified by BamBam using discordantly mapped read pairs, where both reads fully map to the reference genome, but do so in an abnormal, non-reference manner. The putative breakpoints found by BamBam are then refined by a program called bridget using any available split-reads.

Example VI: Refinement of Structural Variation Using Split-Reads

The breakpoints found initially by BamBam are approximate, in that they use fully-mapped reads that, by their nature, cannot overlap the actual junction of the breakpoint, since it represents sequence not present in the reference (or the germline dataset, in the case of a somatic rearrangement). To refine our knowledge of the location of the breakpoint, a program called Bridget was developed, which is summarized in FIG. 4.

Bridget is given the approximate breakpoint found by BamBam and searches for all unaligned reads that are anchored near the putative breakpoint by a fully-mapped mate. Each of these unmapped reads have the potential to be "split reads" that overlaps the rearrangement's breakpoint junction. Localized genomic sequences surrounding both sides of the breakpoint are broken up into a set of unique tiles (currently tile size=16 bp), and a tile database of the tile sequences and their location in the reference genome is built. A similar tile database is constructed for each unaligned read, by breaking up the read into tiles of the same size and noting their location within the read. Comparing the reference tile database and the unaligned tile database, the genomic location of each unaligned tile in the reference is determined. "Dual spanning sets" of these locations are computed by determining the maximal set of tiles that are contiguous in BOTH the reference and unaligned reads, one for each side of the breakpoint.

The minimum and maximum genomic locations of the "dual spanning sets" in reference coordinates precisely determine the breakpoint location, as well as the orientation (or strandedness) of the sequence. With the information describing the left and right boundaries of the breakpoint, the rearranged sequence is fully defined, that is, the left side is defined by (chromosome=chr1, location=1000 bp, strand=forward) and the right side is defined by (chromosome=chr5, location=500,000 bp, strand=reverse). The sequence homology of the breakpoint (that is, a short sequence, such as "CA," observed to be identical on both boundaries of the breakpoint, but is observed only once in the aligned read at the junction of the two sequences) is also determined from these dual spanning sets.

For each unaligned read, the dual spanning sets determine a potential location of the breakpoint. Since each unaligned read may determine slightly different locations for the breakpoint (due to sequence errors near the breakpoint, repetitive reference, etc.), all breakpoint locations determined from the dual spanning sets are used to generate possible junction sequences. All unmapped reads are newly aligned to each of these possible junction sequences and the overall improvement in their alignments is measured against how well the reads aligned to the original sequences. The junction sequence that yields the greatest improvement in alignment scores is judged as the best candidate for the true rearrangement. If this best junction sequence yields little-to-no improvement in the alignment scores, then this junction sequence is discarded as it is unlikely to represent the true rearrangement. In this case, it may also be determined that the lack of split-read confirmation is evidence that the original structural rearrangement found by BamBam could be artifactual.

Figure 4:
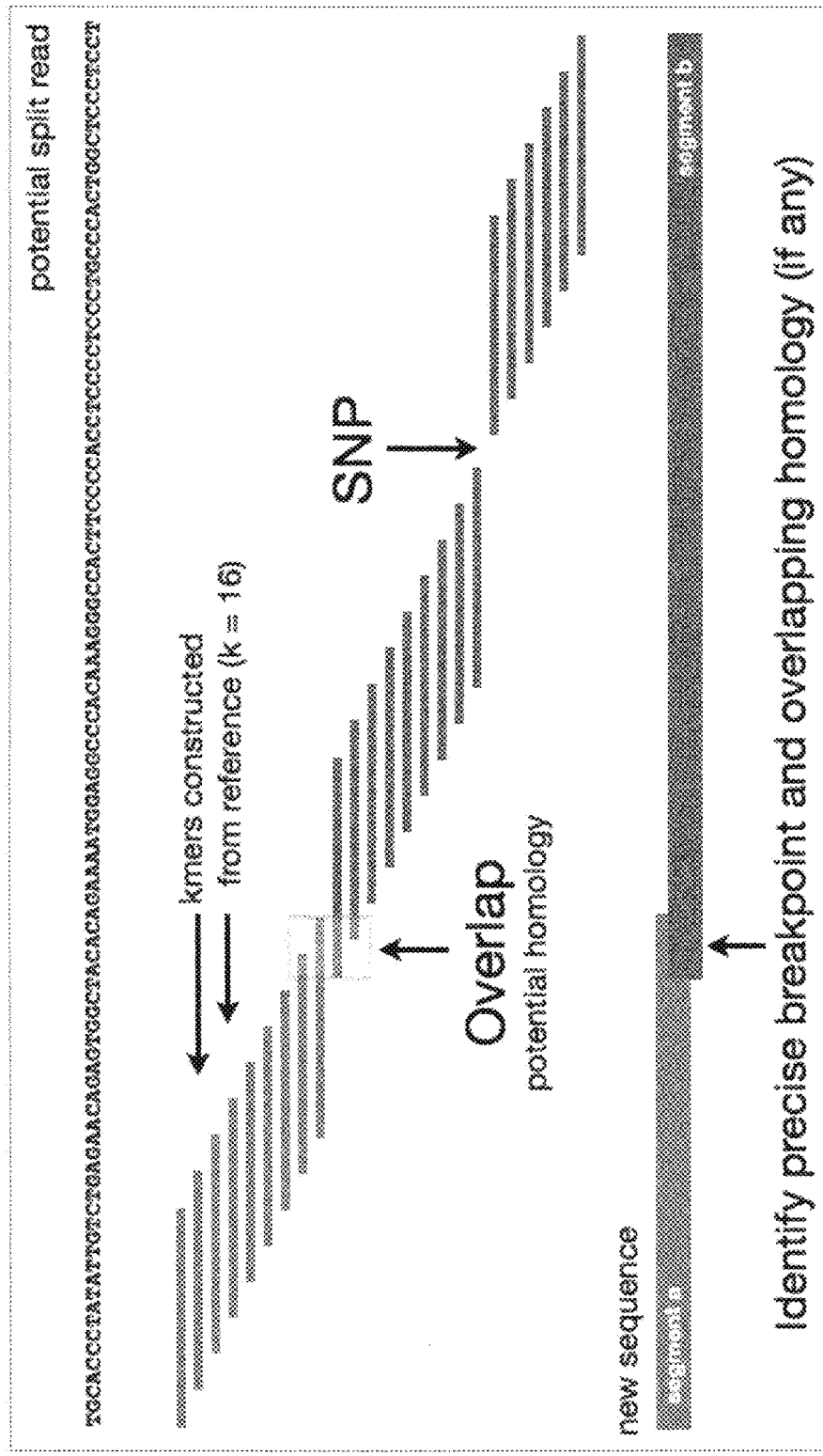
FIG. 4 illustrates an exemplary method to identify the locations in the genome where the structural rearrangement occurred.

FIG. 4 shows an exemplary method to precisely identify the locations in the genome where the structural rearrangement occurred. Tiles (or kmers) are determined for both the potential split read and the reference genome. Dual spanning sets are determined (represent as the thick red and purple boxes on the bottom of this figure), which fully define how to construct the rearranged sequence. Dual spanning sets are robust to sequence errors or SNPs in the split read.

Example VII: Tumor-Specific Genome Browser

Figure 5:
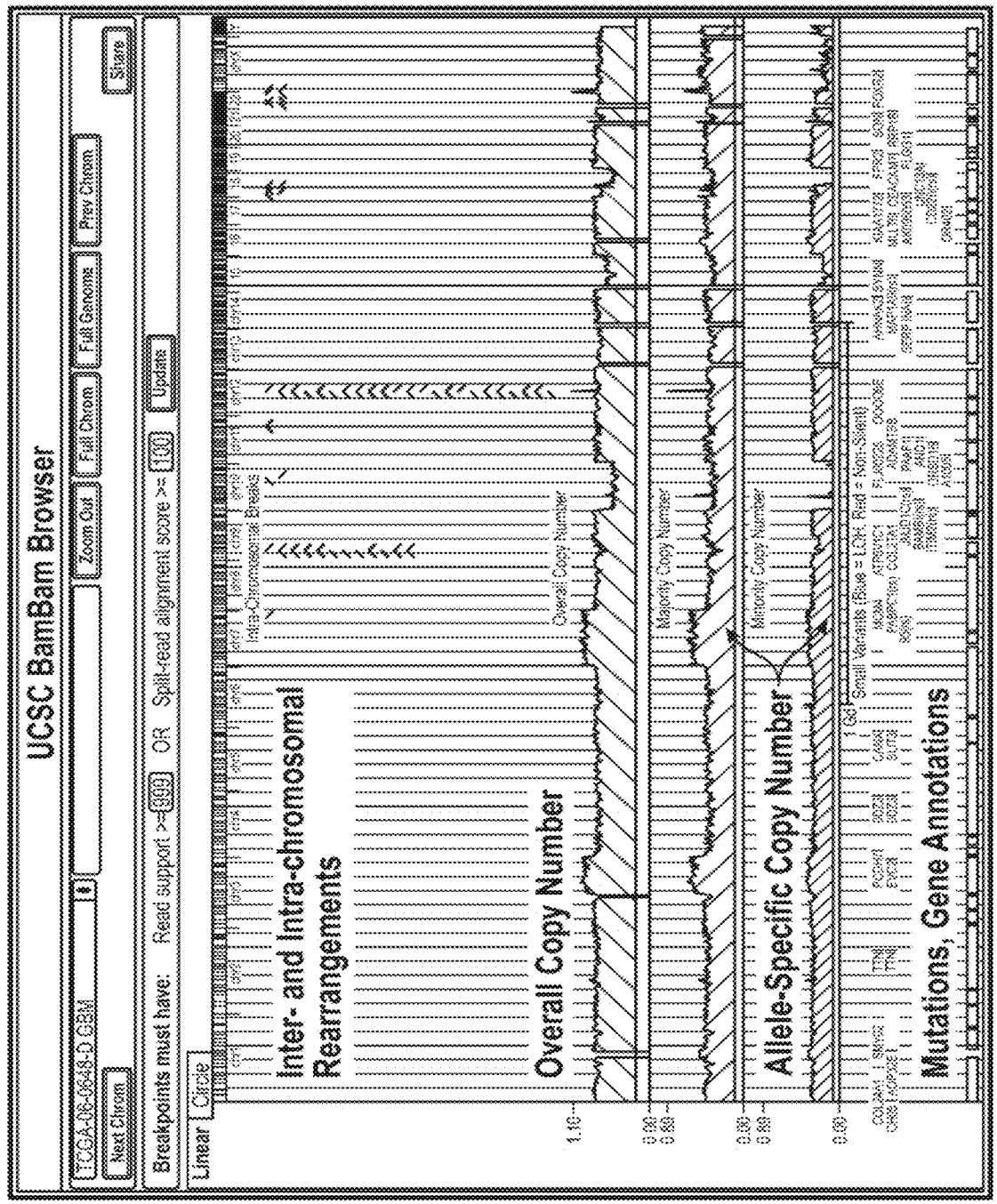
FIG. 5 illustrates an exemplary tumor-specific genome browser.

To visualize all of the results output by BamBam, a tumor genome browser was developed that simultaneously displays all of the genomic variants found in a single tumor sample, versus its matched normal, as shown in FIG. 5. It is capable of displaying overall & allele specific copy number, intra- and inter-chromosomal rearrangements, and mutations and small indels. It displays data in both linear and circular plots, the latter of which being much better suited for display inter-chromosomal rearrangements.

By displaying the data together in a single image, the user can quickly navigate a single sample's data and understand the relationship between changes in copy number and a structural variation. For example, a large intra-chromosomal deletion-type rearrangement should have a concordant drop in copy number in the region between the breakpoints. Also, displaying mutation data with copy number data allows the user to understand if a somatic mutation was subsequently amplified, or if the wild-type allele was deleted in the tumor, both vital datapoints suggesting the importance of the genomic locus in this sample's tumorigenesis.

FIG. 5 shows an exemplary tumor-specific genome browser. The browser shows all of the high-level somatic difference discovered by BamBam in a single image, enabling the synthesis of multiple distinct datasets to give an overall picture of the tumor's genome. The browser is able to zoom into and out of genomic regions rapidly, going from the full genome view, as shown above, to a single base resolution in just a few clicks.

Example VIII: Computational Requirements

Both BamBam and Bridget were written in C, requiring only standard C libraries and the latest SAMtools source code (available from http://samtools.sourceforge.net). It may be run as a single process or broken up into a series of jobs across a cluster (for example, one job per chromosome). Processing a pair of 250 GB BAM files, each containing billions of 100 bp reads, BamBam will finish its whole-genome analysis in approximately 5 hours as a single process, or about 30 minutes on a modest cluster (24 nodes). BamBam's computational requirements were negligible, requiring only enough RAM to store the read data overlapping a single genomic position and enough disk space to store the well-supported variants found in either tumor or germline genomes.

Bridget also had very modest computational requirements. Runtimes on a single machine were typically less than a second, which includes the time necessary to gather the reference sequence and any potential split-reads in the neighborhood of a breakpoint, build tile databases for both reference and split-reads, determine all dual spanning sets, construct potential junction sequences, re-align all split-reads to both reference and each junction sequence, and determine the best junction sequence. Regions that are highly amplified or have high numbers of unmapped reads increase the running time of Bridget, but this may be mitigated by the easy parallelizability of Bridget.

Example IX: Isolation of Genomic DNA

Blood or other tissue samples (2-3 ml) are collected from patients and stored in EDTA-containing tubes at −80° C. until use. Genomic DNA is extracted from the blood samples using a DNA isolation kit according to the manufacturer's instruction (PUREGENE, Gentra Systems, Minneapolis Minn.). DNA purity is measured as the ratio of the absorbance at 260 and 280 nm (1 cm lightpath; $A_{260}/A_{280}$) measured with a Beckman spectrophotometer.

Example X: Identification of SNPs

A region of a gene from a patient's DNA sample is amplified by PCR using the primers specifically designed for the region. The PCR products are sequenced using methods well known to those of skill in the art, as disclosed above. SNPs identified in the sequence traces are verified using Phred/Phrap/Consed software and compared with known SNPs deposited in the NCBI SNP databank.

Example XI: Statistical Analysis

Values are expressed as mean±SD. $\chi_2$ analysis (Web Chi Square Calculator, Georgetown Linguistics, Georgetown University, Washington D.C.) is used to assess differences between genotype frequencies in normal subjects and patients with a disorder. One-way ANOVA with post-hoc analysis is performed as indicated to compare hemodynamics between different patient groups.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A parallel genomic comparative analysis system comprising:
 a computer-readable memory; and
 an sequence analysis engine having at least one processor coupled with the computer-readable memory and configured to:
  identify a genomic position within a reference genome;
  access a first file storing tumor sequence data including reads associated with a tumor tissue;
  access a second file storing matched normal sequence data including reads associated with a matched normal tissue, wherein the first and second files are read at the same time;
  store, in the computer-readable memory, a tumor dataset having tumor read sequences from the first file, where the tumor read sequences overlap the genomic position;
  store, in the computer-readable memory, a matched normal dataset having matched normal read sequences from the second file, where the matched normal read sequences overlap the genomic position, wherein the computer-readable memory is configured to store the tumor dataset and the matched normal dataset simultaneously;

select a tumor genotype and a matched normal genotype that maximize a likelihood as a function of at least one of the tumor read sequences and the matched normal read sequences at the genomic position; and store a difference associated with at least one of the tumor genotype and the matched normal genotype in a device memory.

2. The system of claim 1, wherein the reads associated with at least one of the tumor tissue and the matched normal tissue comprise short reads.

3. The system of claim 1, wherein the reads comprise at least 30 times coverage.

4. The system of claim 1, wherein the sequence analysis engine is further configured to move to a next genomic location as a new genomic position upon processing the reads at the genomic position.

5. The system of claim 1, wherein the sequence analysis engine is further configured to synchronize the first and the second file.

6. The system of claim 5, wherein the reads from the first file and the second file are synchronized with respect to the genomic position.

7. The system of claim 1, wherein the genomic position comprises a common genomic location between the first file and the second file relative to the reference genome.

8. The system of claim 1, wherein the difference is selected from the group consisting of: a somatic variant, a germline variant, a single nucleotide polymorphism, an allele-specific copy number, a loss of heterozygosity, a structural rearrangement, a chromosomal fusion, a mutation, a difference relative to the reference genome, and a breakpoint.

9. The system of claim 1, wherein the likelihood comprises a joint probability between the tumor genotype and the matched normal genotype.

10. The system of claim 1, wherein the sequence analysis engine is further configured to calculate a confidence score of the tumor genotype and the matched normal genotype pair.

11. The system of claim 10, wherein the sequence analysis engine is configured to calculate the confidence score as a posterior probability.

12. The system of claim 10, wherein the sequence analysis engine is further configured to store the confidence score in the device memory with the difference.

13. The system of claim 1, wherein at least one of the first file and the second file comprises at least one of a BAM file and a SAM file.

14. The system of claim 1, wherein the tumor dataset comprises strand information on the tumor read sequences at the genomic position and wherein the sequence analysis engine is further configured to filter tumor variant false positives based on the strand information.

15. The system of claim 1, wherein the matched normal dataset comprises strand information on the matched normal read sequences at the genomic position, and wherein the sequence analysis engine is further configured to filter matched normal variant false positives based on the strand information.

16. The system of claim 1, wherein the tumor dataset comprises a tumor pileup at the genomic position.

17. The system of claim 1, wherein the matched normal dataset comprises a matched normal pileup at the genomic position.

18. The system of claim 1, wherein the difference comprises at least one difference found in at least one of the first file and the second file.

19. A computer implemented method of comparing genomic sequences in parallel, the method comprising:

identifying a genomic position within a reference genome;

accessing, via an sequence analysis engine, a first file storing tumor sequence data including reads associated with a tumor tissue;

accessing, via the sequence analysis engine, a second file storing matched normal sequence data including reads associated with a matched normal tissue, wherein the first and second file are read at the same time;

storing, in a computer-readable memory, a tumor dataset having tumor read sequences from the first file, where the tumor read sequences overlap the genomic position;

storing, in the computer-readable memory, a matched normal dataset having matched normal read sequences from the second file, where the matched normal read sequences overlap the genomic position, wherein the computer-readable memory is configured to store the tumor dataset and the matched normal dataset simultaneously;

selecting, via the sequence analysis engine, a tumor genotype and a matched normal genotype that maximize a likelihood as a function of at least one of the tumor read sequences and the matched normal read sequences at the genomic position; and storing a difference associated with at least one of the tumor genotype and the matched normal genotype in a device memory.

* * * * *